US010104458B2

(12) United States Patent
Boesen et al.

(10) Patent No.: US 10,104,458 B2
(45) Date of Patent: Oct. 16, 2018

(54) ENHANCED BIOMETRIC CONTROL SYSTEMS FOR DETECTION OF EMERGENCY EVENTS SYSTEM AND METHOD

(71) Applicant: BRAGI GmbH, München (DE)

(72) Inventors: Peter Vincent Boesen, München (DE); Lisa Kingscott, München (DE); Rafael Pereira, München (DE)

(73) Assignee: BRAGI GmbH, München (DE)

( * ) Notice: Subject to any disclaimer, the term of this patent is extended or adjusted under 35 U.S.C. 154(b) by 0 days.

(21) Appl. No.: 15/290,519

(22) Filed: Oct. 11, 2016

(65) Prior Publication Data
US 2017/0111725 A1  Apr. 20, 2017

Related U.S. Application Data

(60) Provisional application No. 62/244,152, filed on Oct. 20, 2015.

(51) Int. Cl.
| | | |
|---|---|---|
| *H04R 1/10* | (2006.01) | |
| *A61B 5/024* | (2006.01) | |
| *A61B 5/00* | (2006.01) | |
| *A61B 5/22* | (2006.01) | |
| *G01K 13/00* | (2006.01) | |

(52) U.S. Cl.
CPC ......... *H04R 1/1041* (2013.01); *A61B 5/0008* (2013.01); *A61B 5/02438* (2013.01); *A61B 5/22* (2013.01); *G01K 13/002* (2013.01); *H04R 1/105* (2013.01); *H04R 1/1016* (2013.01); *H04R 2420/07* (2013.01)

(58) Field of Classification Search
CPC .... H04R 1/1041; H04R 1/105; H04R 1/1016; H04R 2420/07; A61B 5/22; A61B 5/0008; A61B 5/02438; G10K 13/002
USPC ........................................................ 381/74
See application file for complete search history.

(56) References Cited

U.S. PATENT DOCUMENTS

| | | |
|---|---|---|
| 3,934,100 A | 1/1976 | Harada |
| 4,150,262 A | 4/1979 | Ono |
| 4,334,315 A | 6/1982 | Ono et al. |

(Continued)

FOREIGN PATENT DOCUMENTS

| | | |
|---|---|---|
| EP | 1017252 A2 | 7/2000 |
| GB | 2074817 | 4/1981 |

(Continued)

OTHER PUBLICATIONS

Announcing the $3,333,333 Stretch Goal (Feb. 24, 2014).

(Continued)

*Primary Examiner* — William A Jerez Lora
(74) *Attorney, Agent, or Firm* — Goodhue, Coleman & Owens, P.C.

(57) ABSTRACT

A system, method and personal area network for communicating utilizing a wireless earpiece. The wireless earpiece is linked with a communications device. Sensor measurements of a condition of a user are performed utilizing sensors of the wireless earpiece. A determination is made whether the sensor measurements exceed one or more thresholds. Communications regarding the sensor measurements are sent from the wireless earpiece to the communications device regarding the condition of the user.

9 Claims, 3 Drawing Sheets

(56) References Cited

U.S. PATENT DOCUMENTS

| | | |
|---|---|---|
| 4,375,016 A | 2/1983 | Harada |
| 4,588,867 A | 5/1986 | Konomi |
| 4,654,883 A | 3/1987 | Iwata |
| 4,682,180 A | 7/1987 | Gans |
| 4,791,673 A | 12/1988 | Schreiber |
| 4,865,044 A | 9/1989 | Wallace et al. |
| 5,191,602 A | 3/1993 | Regen et al. |
| 5,201,007 A | 4/1993 | Ward et al. |
| 5,280,524 A | 1/1994 | Norris |
| 5,295,193 A | 3/1994 | Ono |
| 5,298,692 A | 3/1994 | Ikeda et al. |
| 5,343,532 A | 8/1994 | Shugart |
| 5,363,444 A | 11/1994 | Norris |
| 5,497,339 A | 3/1996 | Bernard |
| 5,606,621 A | 2/1997 | Reiter et al. |
| 5,613,222 A | 3/1997 | Guenther |
| 5,692,059 A | 11/1997 | Kruger |
| 5,721,783 A | 2/1998 | Anderson |
| 5,749,072 A | 5/1998 | Mazurkiewicz et al. |
| 5,771,438 A | 6/1998 | Palermo et al. |
| 5,802,167 A | 9/1998 | Hong |
| 5,929,774 A | 7/1999 | Charlton |
| 5,933,506 A | 8/1999 | Aoki et al. |
| 5,949,896 A | 9/1999 | Nageno et al. |
| 5,987,146 A | 11/1999 | Pluvinage et al. |
| 6,021,207 A | 2/2000 | Puthuff et al. |
| 6,054,989 A | 4/2000 | Robertson et al. |
| 6,081,724 A | 6/2000 | Wilson |
| 6,094,492 A | 7/2000 | Boesen |
| 6,111,569 A | 8/2000 | Brusky et al. |
| 6,112,103 A | 8/2000 | Puthuff |
| 6,157,727 A | 12/2000 | Rueda |
| 6,167,039 A | 12/2000 | Karlsson et al. |
| 6,181,801 B1 | 1/2001 | Puthuff et al. |
| 6,208,372 B1 | 3/2001 | Barraclough |
| 6,275,789 B1 | 8/2001 | Moser et al. |
| 6,339,754 B1 | 1/2002 | Flanagan et al. |
| 6,408,081 B1 | 6/2002 | Boesen |
| D464,039 S | 10/2002 | Boesen |
| 6,470,893 B1 | 10/2002 | Boesen |
| D468,299 S | 1/2003 | Boesen |
| D468,300 S | 1/2003 | Boesen |
| 6,542,721 B2 | 4/2003 | Boesen |
| 6,560,468 B1 | 5/2003 | Boesen |
| 6,654,721 B2 | 11/2003 | Handelman |
| 6,664,713 B2 | 12/2003 | Boesen |
| 6,694,180 B1 | 2/2004 | Boesen |
| 6,718,043 B1 | 4/2004 | Boesen |
| 6,738,485 B1 | 5/2004 | Boesen |
| 6,748,095 B1 | 6/2004 | Goss |
| 6,754,358 B1 | 6/2004 | Boesen et al. |
| 6,784,873 B1 | 8/2004 | Boesen et al. |
| 6,823,195 B1 | 11/2004 | Boesen |
| 6,852,084 B1 | 2/2005 | Boesen |
| 6,879,698 B2 | 4/2005 | Boesen |
| 6,892,082 B2 | 5/2005 | Boesen |
| 6,920,229 B2 | 7/2005 | Boesen |
| 6,952,483 B2 | 10/2005 | Boesen et al. |
| 6,987,986 B2 | 1/2006 | Boesen |
| 7,136,282 B1 | 11/2006 | Rebeske |
| 7,203,331 B2 | 4/2007 | Boesen |
| 7,209,569 B2 | 4/2007 | Boesen |
| 7,215,790 B2 | 5/2007 | Boesen et al. |
| 7,463,902 B2 | 12/2008 | Boesen |
| 7,508,411 B2 | 3/2009 | Boesen |
| 7,983,628 B2 | 7/2011 | Boesen |
| 8,140,357 B1 | 3/2012 | Boesen |
| 2001/0005197 A1 | 6/2001 | Mishra et al. |
| 2001/0027121 A1 | 10/2001 | Boesen |
| 2001/0056350 A1 | 12/2001 | Calderone et al. |
| 2002/0002413 A1 | 1/2002 | Tokue |
| 2002/0007510 A1 | 1/2002 | Mann |
| 2002/0010590 A1 | 1/2002 | Lee |
| 2002/0030637 A1 | 3/2002 | Mann |
| 2002/0046035 A1 | 4/2002 | Kitahara et al. |
| 2002/0057810 A1 | 5/2002 | Boesen |
| 2002/0076073 A1 | 6/2002 | Taenzer et al. |
| 2002/0118852 A1 | 8/2002 | Boesen |
| 2003/0065504 A1 | 4/2003 | Kraemer et al. |
| 2003/0100331 A1 | 5/2003 | Dress et al. |
| 2003/0104806 A1 | 6/2003 | Ruef et al. |
| 2003/0115068 A1 | 6/2003 | Boesen |
| 2003/0125096 A1 | 7/2003 | Boesen |
| 2003/0218064 A1 | 11/2003 | Conner et al. |
| 2004/0070564 A1 | 4/2004 | Dawson et al. |
| 2004/0160511 A1 | 8/2004 | Boesen |
| 2005/0043056 A1 | 2/2005 | Boesen |
| 2005/0125320 A1 | 6/2005 | Boesen |
| 2005/0148883 A1 | 7/2005 | Boesen |
| 2005/0165663 A1 | 7/2005 | Razumov |
| 2005/0196009 A1 | 9/2005 | Boesen |
| 2005/0251455 A1 | 11/2005 | Boesen |
| 2005/0266876 A1 | 12/2005 | Boesen |
| 2006/0029246 A1 | 2/2006 | Boesen |
| 2006/0074671 A1 | 4/2006 | Farmaner et al. |
| 2006/0074808 A1 | 4/2006 | Boesen |
| 2006/0159298 A1* | 7/2006 | von Dombrowski .. H04R 25/48 381/330 |
| 2008/0254780 A1 | 10/2008 | Kuhl et al. |
| 2008/0267416 A1* | 10/2008 | Goldstein ............ H04R 1/1091 381/56 |
| 2011/0137141 A1* | 6/2011 | Razoumov ........... A61B 5/0002 600/316 |
| 2013/0010657 A1* | 1/2013 | Hannosh ............... H04M 9/082 370/280 |
| 2013/0281795 A1* | 10/2013 | Varadan ............. A61B 5/02055 600/301 |
| 2013/0316649 A1* | 11/2013 | Newham ............... H04W 88/04 455/41.2 |
| 2014/0088454 A1* | 3/2014 | Mack ....................... A61B 5/11 600/553 |
| 2015/0035680 A1 | 2/2015 | Li et al. |
| 2015/0245795 A1 | 9/2015 | Rennaker |

FOREIGN PATENT DOCUMENTS

| | | |
|---|---|---|
| JP | 06292195 | 10/1998 |
| WO | 2010099190 A3 | 1/2011 |
| WO | 2014043179 A2 | 3/2014 |
| WO | 2015110577 A1 | 7/2015 |
| WO | 2015110587 A1 | 7/2015 |

OTHER PUBLICATIONS

BRAGI Is On Facebook (2014).
BRAGI Update—Arrival Of Prototype Chassis Parts—More People—Awesomeness (May 13, 2014).
BRAGI Update—Chinese New Year, Design Verification, Charging Case, More People, Timeline(Mar. 6, 2015).
BRAGI Update—First Sleeves From Prototype Tool—Software Development Kit (Jun. 5, 2014).
BRAGI Update—Let's Get Ready To Rumble, A Lot To Be Done Over Christmas (Dec. 22, 2014).
BRAGI Update—Memories From April—Update On Progress (Sep. 16, 2014).
BRAGI Update—Memories from May—Update On Progress—Sweet (Oct. 13, 2014).
BRAGI Update—Memories From One Month Before Kickstarter—Update On Progress (Jul. 10, 2014).
BRAGI Update—Memories From The First Month of Kickstarter—Update on Progress (Aug. 1, 2014).
BRAGI Update—Memories From The Second Month of Kickstarter—Update On Progress (Aug. 22, 2014).
BRAGI Update—New People @BRAGI—Prototypes (Jun. 26, 2014).
BRAGI Update—Office Tour, Tour To China, Tour to CES (Dec. 11, 2014).
BRAGI Update—Status On Wireless, Bits and Pieces, Testing-Oh Yeah, Timeline(Apr. 24, 2015).
BRAGI Update—The App Preview, The Charger, The SDK, BRAGI Funding and Chinese New Year (Feb. 11, 2015).

(56) References Cited

OTHER PUBLICATIONS

BRAGI Update—What We Did Over Christmas, Las Vegas & CES (Jan. 19, 2014).
BRAGI Update—Years of Development, Moments of Utter Joy and Finishing What We Started(Jun. 5, 2015).
BRAGI Update—Alpha 5 and Back To China, Backer Day, On Track(May 16, 2015).
BRAGI Update—Beta2 Production and Factory Line(Aug. 20, 2015).
BRAGI Update—Certifications, Production, Ramping Up (Nov. 13, 2015).
BRAGI Update—Developer Units Shipping and Status(Oct. 5, 2015).
BRAGI Update—Developer Units Started Shipping and Status (Oct. 19, 2015).
BRAGI Update—Developer Units, Investment, Story and Status(Nov. 2, 2015).
BRAGI Update—Getting Close(Aug. 6, 2014).
BRAGI Update—On Track, Design Verification, How It Works and What's Next(Jul. 15, 2015).
BRAGI Update—On Track, On Track and Gems Overview (Jun. 24, 2015).
BRAGI Update—Status On Wireless, Supply, Timeline and Open House@BRAGI(Apr. 1, 2015).
BRAGI Update—Unpacking Video, Reviews On Audio Perform and Boy Are We Getting Close(Sep. 10, 2015).
Last Push Before The Kickstarter Campaign Ends on Monday 4pm CET (Mar. 28, 2014).
Staab, Wayne J., et al., "A One-Size Disposable Hearing Aid is Introduced", The Hearing Journal 53(4):36-41) Apr. 2000.
Stretchgoal—It's Your Dash (Feb. 14, 2014).
Stretchgoal—The Carrying Case for The Dash (Feb. 12, 2014).
Stretchgoal—Windows Phone Support (Feb. 17, 2014).
The Dash + The Charging Case & The BRAGI News (Feb. 21, 2014).
The Dash—A Word From Our Software, Mechanical and Acoustics Team + An Update (Mar. 11, 2014).
Update From BRAGI—$3,000,000—Yipee (Mar. 22, 2014).
International Search Report & Written Opinion, PCT/EP2016/075118 (dated Mar. 7, 2017).

* cited by examiner

ENHANCED BIOMETRIC CONTROL SYSTEMS FOR DETECTION OF EMERGENCY EVENTS SYSTEM AND METHOD

PRIORITY STATEMENT

This application claims priority to U.S. Provisional Patent Application 62/244,152, filed on Oct. 20, 2015, and entitled Enhanced Biometric Control Systems For Detection Of Emergency Events System and Method, hereby incorporated by reference in its entirety.

BACKGROUND

I. Field of the Disclosure

The illustrative embodiments relate to wireless earpieces. More specifically, but not exclusively, the illustrative embodiments relate to wireless earpieces for monitoring user biometrics and actions.

II. Description of the Art

The growth of wearable devices is increasing exponentially. This growth is fostered by the decreasing size of microprocessors, circuitry boards, Chips, and other components. In some cases, wearable devices may obtain biometric data. An important aspect of biometric data is determining user safety, activities, and conditions. In some cases, determining and reporting the user's biometrics and condition may be difficult because of location, position, effects of the user's condition, or user activity.

SUMMARY OF THE DISCLOSURE

One embodiment of the illustrative embodiments provides a system, method and personal area network for communicating utilizing a wireless earpiece. The wireless earpiece is linked with a communications device. Sensor measurements of a condition of a user are performed utilizing sensors of the wireless earpiece. A determination is made whether the sensor measurements exceed one or more thresholds. Communications regarding the sensor measurements are sent from the wireless earpiece to the communications device regarding the condition of the user. Another embodiment provides wireless earpieces including a processor and a memory storing a set of instructions. The set of instructions are executed to perform the method described.

Another embodiment provides a wireless earpiece. The wireless earpiece may include a frame for fitting in an ear of a user. The wireless earpiece may also include a logic engine controlling functionality of the wireless earpiece. The wireless earpiece may also a number of sensors receiving biometric information from the user. The wireless earpiece may also include a transceiver communicating with at least a wireless device. The number of sensors take sensor measurements of a condition of a user. The logic engine determines whether the sensor measurements exceed one or more thresholds. The transceiver sends communications regarding the sensor measurements from the wireless earpiece to the wireless device.

BRIEF DESCRIPTION OF THE DRAWINGS

Illustrated embodiments of the present invention are described in detail below with reference to the attached drawing figures, which are incorporated by reference herein, and where.

DETAILED DESCRIPTION OF THE DISCLOSURE

The illustrative embodiments provide a system, method, and personal area network for determining a user's condition and associated biometrics. The user's information may then be communicated to one or more additional wireless earpieces, computing, or communications devices. In one embodiment, the wireless earpieces may be part of a personal area network. The wireless earpieces may be utilized to control, communicate, manage, or interact with a number of other wearable devices, such as smart, glasses, helmets, smart glass, watches or wrist bands, chest straps, implants, displays, clothing, or so forth. A personal area network is a network for data transmissions among devices, such as personal computing, communications, camera, vehicles entertainment, and medical devices. The personal area network may utilize any number of wired, wireless, or hybrid configurations and may be stationary or dynamic. For example, the personal area network may utilize wireless network protocols or standards, such as INSTEON, IrDA, Wireless USB, Bluetooth, Z-Wave, ZigBee, Wi-Fi, ANT+ or other applicable radio frequency signals. In one embodiment, the personal area network may move with the user.

The wireless earpieces may include any number of sensors for receiving user biometrics, such as pulse rate, blood oxygenation, temperature, calories expended, voice and audio output, and orientation (e.g., body, head, etc.). The sensors may also determine the user's location, position, velocity, impact levels, and so forth. The sensors may also receive user input and convert the user input into commands or selections made across the personal devices of the personal area network. For example, the user input detected by the wireless earpieces may include voice commands, head motions, finger taps, finger swipes, motions or gestures, or other user inputs sensed by the wireless earpieces. The user input may be determined and converted into commands that may be sent to one or more external devices, such as a tablet computer, smart phone, or so forth.

Figure 1:
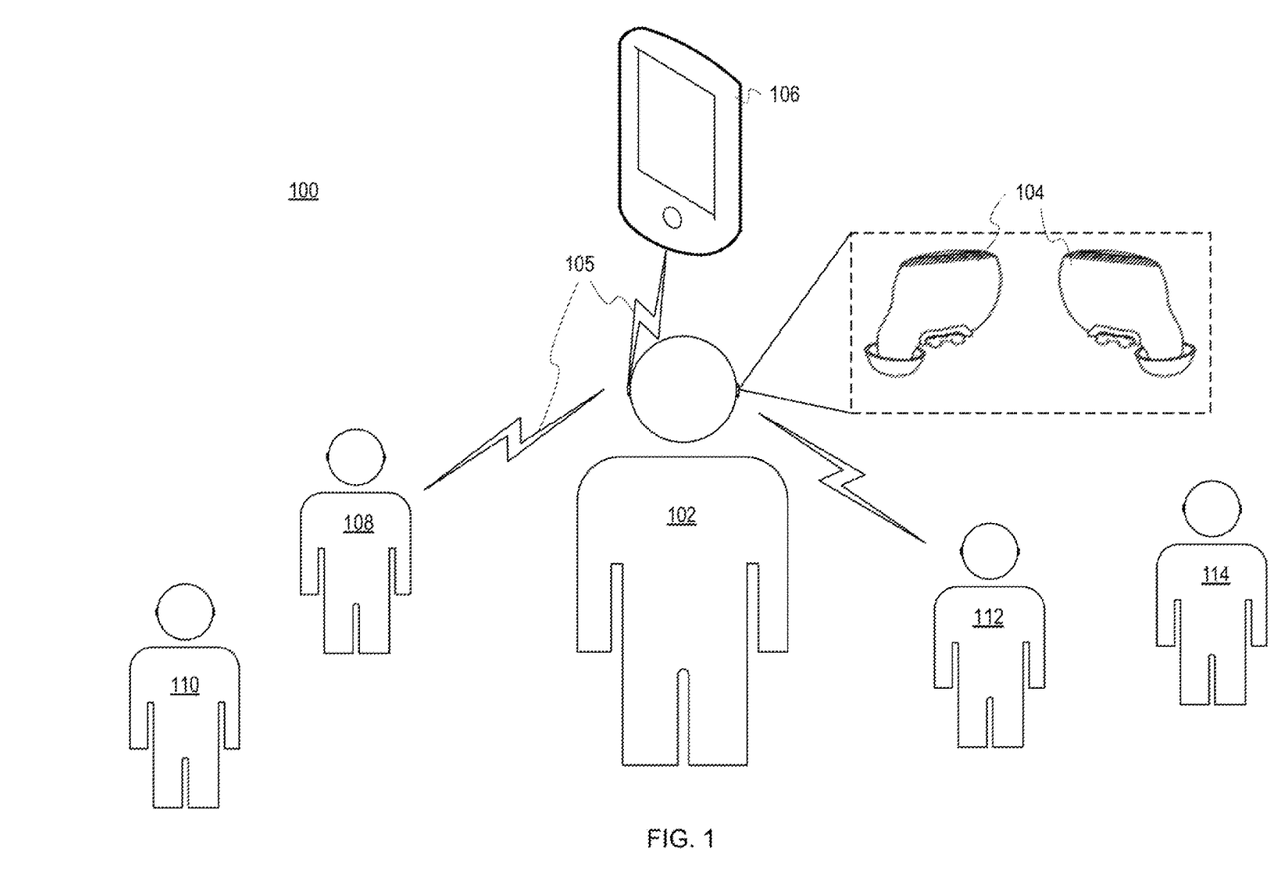
FIG. 1 is a pictorial representation of a communication system in accordance with an illustrative embodiment.

FIG. 1 is a pictorial representation of a communication system 100 in accordance with an illustrative embodiment. In one embodiment, the communication system 100 may represent a personal area network utilized by one or more users. The communication system 100 may also represent any number of systems, environments, or networks in which a user may utilize the described devices and components.

In one embodiment, the communication system 100 may include a user 102 utilizing wireless earpieces 104 and communicating with a communications device 106. The wireless earpieces 104 may communicate with the communications device 106 through a wireless signal 105. The reference to the user 102 may further represent the user utilizing the wireless earpieces 104. Likewise, each of users 108, 110, 112, and 114 may also be utilizing wireless earpieces similar to the wireless earpieces 104.

The wireless earpieces 104 are shown as worn and separately from their positioning within the ears of the user 102 for purposes of visualization. In one embodiment, the wireless earpieces 104 include a frame shaped to fit substantially within the ear of the user 102. The frame is a support structure that at least partially encloses and houses the electronic components of the wireless earpieces 104. The frame may include one or more sleeves configured to fit the inside of the ear of the user 102. The sleeves may have extremely tight tolerances to lit user 102. In another embodiment, the sleeves may be custom built, in some applications, temporary adhesives or securing mechanisms (e.g., clamps, straps, extenders, etc.) may be utilized to ensure that the wireless earpieces 104 remain in the ears of the user 102 even during the most rigorous and physical activities. For example, the wireless earpieces 104 may be utilized during water polo matches, football games, triathlons, or soccer matches. The wireless earpieces 104 may be configured to play music or audio, receive and make phone calls or other communications, determine ambient environmental conditions (e.g., temperature, altitude, location, speed, heading, etc.), read user biometrics (e.g., heart rate, motion, temperature, sleep, blood oxygenation, voice output, calories burned, forces experienced, etc.), and receive user input, feedback, or instructions.

In one embodiment, the users 102, 108-114 may represent a group, team, or association of individuals participating in a common activity, event, game, or other happening. For example, the users 102, 108-114 may represent teammates. The wireless earpieces 116 utilized by the users 102, 108-114 may be fully enabled or may have partial functionality during the activity. For example, the users 102, 108-114 may be football players and the communications functions of the wireless earpieces 116 may only be activated for a quarterback and a coach of the team (the remaining devices perform sensory operations only and allow sound of the playing environment to be passed through or amplified to the user). The remaining wireless earpieces 116 may be utilized to monitor the users' conditions to ensure their vitals are within satisfactory ranges and that any tackles or hits do not result in forces sufficient to injure or concuss the specific players. As a result of the communications system 100, allowed communications may be enhanced while still monitoring the health and safety of the users 102, 108-114.

In another embodiment, the users 102, 108-114 may represent a team working jointly on a project event, or operation. The users 102, 108-114 may be able to communicate with one another directly or indirectly utilizing the wireless earpieces 116. The communications system 100 may include any number of networks, repeaters, or extenders for extending the range and accessibility of the wireless earpieces. The communications device 106 may receive biometric information for each of the users 102, 108-114 enabling a single person or group too monitor the status and condition of the users 102, 108-114. In other embodiments, the biometric data acquired for the users 102, 108-114 for the corresponding wireless earpieces 116 may be sent remotely to any number of devices or systems. For example, the data may be archived in one or more remote servers and databases for subsequent retrieval though a cloud network and interface. The information reported by the wireless earpieces 116 may be sent to emergency medical services, relatives of each of the users 102, 108-114, or other designated contacts. For example, a potentially dangerous impact detected by the wireless earpieces 104 for the user 102 may be reported to a coach utilizing the communications device 106 as well as the parents or designated guardians of the user 102.

The wireless earpieces 116 may be utilized for early detection and treatment of the users 102, 108-114 based on an injury (e.g., head strike, hit, crash, accident, fall, etc.) or other detected health event (e.g., overheating, hypothermia, heart attack, stroke, seizure, asthma attack, electrocution, etc.). The wireless earpieces 116 may also detect a particular sound pattern or audio, such as a user groaning, screaming, or other audio event that may be associated with a potential injury or health event. The wireless earpieces 116 may include a library stored within their respective memories including one or more thresholds or data, for determining whether the user may be experiencing an injury or health event.

The devices of the communication system 100 may include any number of devices, components, or so forth that may communicate with each other directly or indirectly through a wireless (or wired) connection, signal, or link, such as the wireless signals 105. The communications system 100 may be a network and may include any number of network components and devices, such as routers, servers, signal extenders, intelligent network devices, computing devices, or so forth. In one embodiment, the network of the communications system 100 represents a personal area network as previously disclosed. Communications, such as the wireless signals 105, within the communication system 100 may occur through the network or may occur directly between devices, such as the wireless earpieces 104 and the communications device 106 (e.g., direct communication of the wireless signal 105) or between the wireless earpieces 102 and the wireless device 128 (indirect communication through a Wi-Fi network utilizing the wireless signal 105). In one embodiment, the communications system 100 may communicate with or include a wireless network, such as a Wi-Fi, cellular (e.g. 3G, 4G, 5G, PCS, GSM, etc.), Bluetooth, or other radio frequency network. The communications system 100 may also communicate with any number of hard wired networks, such as local area networks, coaxial networks, fiber-optic networks, or so forth. Communications within the communication system 100 may be operated by one or more users, service providers, or network providers.

As noted, both the wireless earpieces 116 as well as wearable or implantable devices utilized by the users 102, 108-114 may include a number of sensors including touch sensors, optical sensors, pulse oximeters, microphones, ear bone microphones, accelerometers, gyroscopes, global positioning chips, thermometers, and so forth for detecting the biometrics, motion, location, and activities of the user. The information may be utilized to coordinate the audio, video, text, and graphical information presented to the user 116 (as well as the communications device 106) by the respective wireless earpieces 116. In one embodiment, the user 102 may program the wireless earpieces 104 to perform specific activities in response to a specific biometric reading, user motion, command or audio signal, or other action. For examples, the user 102 may configure the wireless earpieces 102 (directly or indirectly through a user interface of a computing device communicating with the wireless earpieces 104) to send a concussion alert in response to sensing forces above a specified level applied to the head of the user 102

Any number of user and environmental conditions may be utilized to generate alerts or other communications. The alerts may also be played audibly to the users 102, 108-114. For example, the user may be played an alert indicating "you may be overheating, consider drinking water and taking a break", or "you just experience a significant jolt, do you have a concussion?" The wireless earpieces 116 as well as the communications device 106 may include logic for automatically calling emergency services in response to events, such as the user's 102, pulse stopping or slowing significantly. As a result, the communication system 100 may be adapted to the needs and desires of the user 101.

In one embodiment, the communications device 106 may utilize short-range or long-range wireless communications to communicate with the wireless earpieces 116 through the wireless signal. 105 or devices of the communications system 100 through the wireless signal 105. For example, the communications device 106 may include a Bluetooth and cellular transceiver within the embedded logical components. For example, the wireless signal 106 may be a Bluetooth, Wi-Fi, Zigbee, Ant+, or other short range wireless communication.

The communications device 106 may represent any number of wireless or wired electronic communications or computing devices, such as smart phones, laptops, desktop computers, control systems, tablets, displays, gaming devices, music players, personal digital assistants, vehicle systems, or so forth. The communications device 106 may communicate utilizing any number of wireless connections, standards, or protocols (e.g., near field communications, Bluetooth, Wi-Fi, wireless Ethernet, etc.). For example, the communications device 106 may be a touch screen cellular phone that communicates with the wireless earpieces 116 utilizing Bluetooth communications. The communications device 106 may implement and utilize any number of operating systems, kernels, instructions, or applications that may make use of the sensor data or user input received from the wireless earpieces 116. For example, the communications device 106 may represent any number of android, ADS, Windows, open platforms, or other systems. Similarly, the communications device 106 or the wireless earpieces 116 may include a number of applications that utilize the user input, biometric data, and other feedback from the wireless earpieces 116 to display applicable information and data, control the applications, play audible or tactile alerts, or make other selections. For example, biometric information (including, high, low, average, or other values) may be processed by the wireless earpieces 116 or the communications device 106 to display experienced forces, heart rate, blood oxygenation, altitude, speed, distance traveled, calories burned, or other applicable information.

In one embodiment, the wireless device 106 may include any number of input components and sensors (e.g., similar to those described with regard to the wireless earpieces 116) that may be utilized to augment the input and sensor readings of the wireless earpieces 116. For example, a microphone of the wireless device 106 may determine an amount and type of ambient noise. The noise may be analyzed and utilized to filter the sensor readings made by the wireless earpieces 116 to maximize the accuracy and relevance of the sensor measurements of the wireless earpieces 116. For example, the wireless earpieces 116 may adjust the microphone sensitivity or filter out background noise based on measurements performed by the communications device 106. Filtering, tuning, and adaptation for the sensor measurements may be made for signal noise, electronic noise, or acoustic noise, all of which are applicable in the communication system 100. Sensor measurements made by either the wireless earpieces 116 or communications device 106 may be communicated with one another in the communication system 100. As noted, the communications device 106 is representative of any number of personal computing, communications, exercise, medical, or entertainment devices that may communicate with the wireless earpieces 116.

With respect to the wireless earpieces 116, sensor measurements or user input may refer to measurements made by one or both of the wireless earpieces 116 in a set. For example, the right wireless earpiece of wireless earpieces 104 may determine that the user may have experienced a concussive event even though the event was not detected by the left wireless earpiece of wireless earpieces 104. The wireless earpieces 104 may also switch back and forth between sensors of the left and right wireless earpiece in response to varying noise, errors, or more accurate signals for both of the wireless earpieces 104. As a result, the clearest sensor signal may be utilized at any given time. In one embodiment, the wireless earpieces 104 may switch sensor measurements in response to the sensor measurements exceeding or dropping below a specified threshold.

The user 102 may also be wearing or carrying any number of sensor-enabled devices, such as heart rate monitors, pacemakers, smart glasses, smart watches or bracelets (e.g., Apple watch, Fitbit, etc.), or other sensory devices that may be worn, attached to, or integrated with the user 102. The data and information from the external sensor devices may be communicated to the wireless earpieces 104. In another embodiment, the data and information from the external sensor devices may be utilized to perform additional processing of the information sent from the wireless earpieces 104 to the communications device 106.

The sensors of the wireless earpieces 104 may be positioned at enantiomeric locations. For example, a number of colored light emitting diodes may be positioned to provide variable data and information, such as heart rate, respiratory rate, and so forth. The data gathered by the LED arrays may be sampled and used alone or in aggregate with other sensors. As a result, sensor readings may be enhanced and strengthened with additional data.

In another embodiment, the wireless earpieces 102 may represent or communicate with other wireless devices that may be ingested or implanted into a user. For example, the described electronics may be endoscopic pills, pacemakers, tracking devices, contact lenses, oral implants, bone implants, artificial organs, or so forth.

Figure 2:
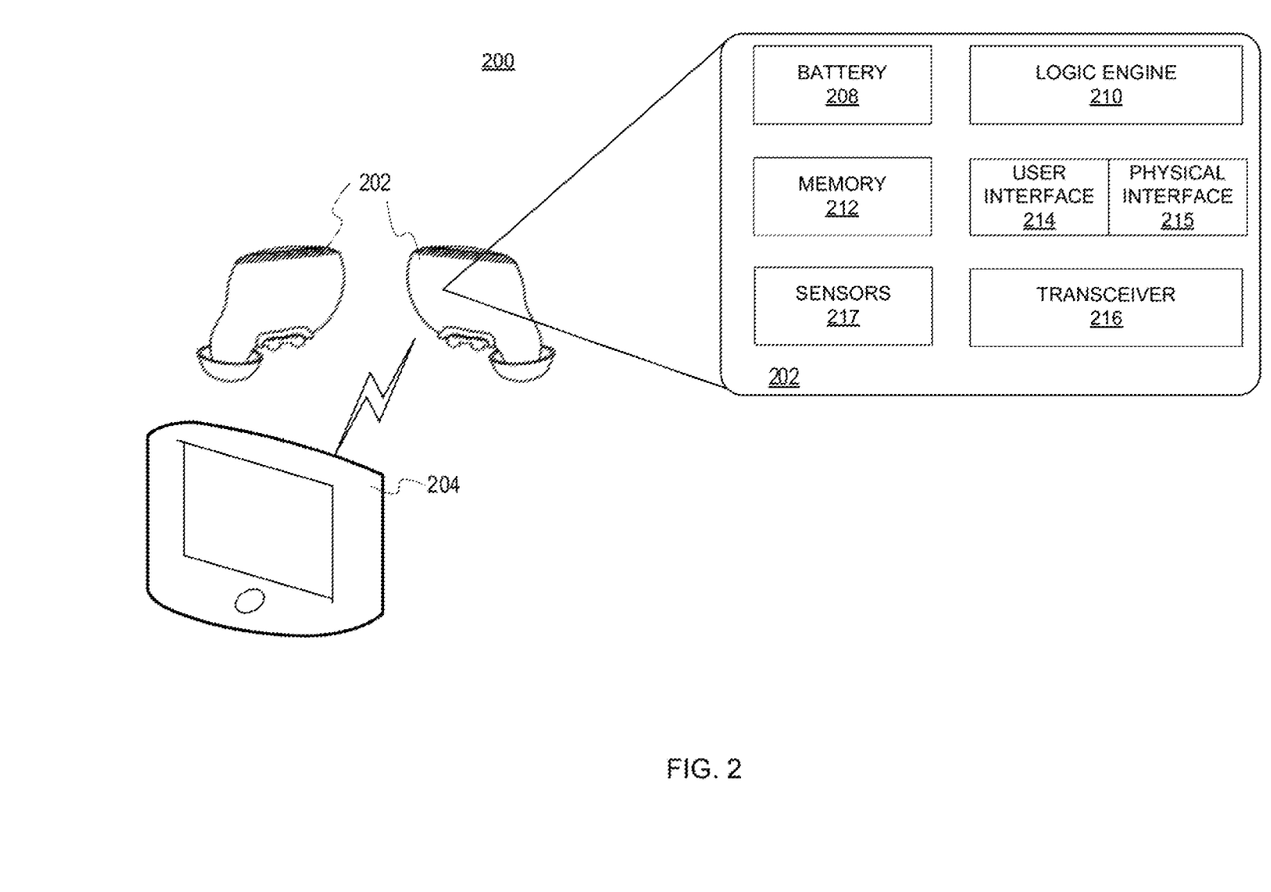
FIG. 2 is a block diagram of wireless earpieces in accordance with an illustrative embodiment.

FIG. 2 is a block diagram of a wireless earpiece system 200 in accordance with an illustrative embodiment. In one embodiment, the wireless earpiece system 200 may include wireless earpieces 202 (described collectively rather than individually). In one embodiment, the wireless earpiece system 200 may enhance communications and functionality of the wireless earpieces 202.

As shown, the wireless earpieces 202 may be wireless linked to a computing device 204. For example, the computing device 204 may represent a wireless tablet computer. User input and commands may be received from either the wireless earpieces 202 or the computing device 204 for implementation on either of the devices of the wireless earpiece system 200 for other externally connected devices). As previously noted, the wireless earpieces 102 may be referred to or described herein as a pair (wireless earpieces) or singularly (wireless earpiece). The description may also refer to components and functionality of each of the wireless earpieces 202 collectively or individually.

In some embodiments, the computing device 204 may act as a logging tool for receiving information, data, or measurements made by the wireless earpieces 202. For example, the computing device 204 may download data from the wireless earpieces 202 in real-time. As a result, the computing device 204 may be utilized to store, display, and synchronize data for the wireless earpieces 202. For example, the computing device 204 may display pulse, oxygenation, distance, calories burned, and so forth as measured by the wireless earpieces 202. The computing device 204 may be configured to receive and display alerts that indicate a specific health event or condition has been met. For example, if the forces applied to the sensors 217 (e.g., accelerometers) indicates that the user may have experienced a concussion or serious trauma, the wireless earpieces 202 may generate and send a message to the computing device 204. The wireless earpieces 202 and the computing device 204 may have any number of electrical configurations, shapes, and colors and may include various circuitry, connections, and other components.

In one embodiment, the wireless earpieces 202 may include a battery 208, a logic engine 210, a memory 212, a user interface 214, a physical interface 215, a transceiver 216, and sensors 217. The computing device 204 may have any number of configurations and include components and features as are known in the art.

The battery 208 is a power storage device configured to power the wireless earpieces 202. Likewise, the battery 208 is a power storage device configured to power the computing device 204. In other embodiments, the battery 208 may represent a fuel cell, thermal electric generator, piezo electric charger, solar charger, ultra-capacitor, or other existing or developing power storage technologies.

The logic engine 210 is the logic that controls the operation and functionality of the wireless earpieces 202. The logic engine 210 may include circuitry, chips, and other digital logic. The logic engine 210 may also include programs, scripts, and instructions that may be implemented to operate the logic engine 210. The logic engine 210 may represent hardware, software, firmware, or any combination thereof. In one embodiment, the logic engine 210 may include one or more processors. The logic engine 210 may also represent an application specific integrated circuit (ASIC) or field programmable gate array (FPGA). The logic engine 210 may utilize information from the sensors 217 to determine the biometric information, data, and readings of the user. The logic engine 210 may utilize this information and other criteria to inform the user of the biometrics (e.g., audibly, through an application of a connected device, tactilely, etc.) as well as communicate with the computing device 204 through the transceiver 216.

The logic engine 210 may also process user input to determine commands implemented by the wireless earpieces 202 or sent to the computing device 204 through the transceiver 216. Specific actions may be associated with biometric data thresholds. For example, the logic engine 210 may implement a macro allowing the user to associate biometric data as sensed by the sensors 217 with specified commands, alerts, and so forth. For example, if the temperature of the user is above or below high and low thresholds, an audible alert may be played to the user and a communication sent to the computing device 204.

In one embodiment, a processor included in the logic engine 210 is circuitry or logic, enabled to control execution of a set of instructions. The processor may be one or more microprocessors, digital signal processors, application-specific integrated circuits (ASIC), central processing units, or other devices suitable for controlling an electronic device including one or more hardware and software elements, executing software, instructions, programs, and applications, converting and processing signals and information, and performing other related tasks.

The memory 212 is a hardware element, device, or recording media configured to store data or instructions for subsequent retrieval or access at a later time. The memory 212 may represent static or dynamic memory. The memory 212 may include a hard disk, random access memory, cache, removable media drive, mass storage, or configuration suitable as storage for data, instructions, and information. In one embodiment, the memory 212 and the logic engine 210 may be integrated. The memory may use any type of volatile or non-volatile storage techniques and mediums. The memory 212 may store information related to the status of a user, wireless earpieces 202, computing device 204, and other peripherals, such as a wireless device, smart glasses, smart watch, smart case for the wireless earpieces 202, wearable device, and so forth. In one embodiment, the memory 212 may display instructions, programs, drivers, or an operating system for controlling the user interface 214 including one or more LEDs or other light emitting components, speakers, tactile generators (e.g., vibrator), and so forth. The memory 212 may also store the thresholds, conditions, or biometric data (e.g., biometric and data library) associated with biometric events.

The transceiver 216 is a component comprising both a transmitter and receiver which may be combined and share common circuitry on a single housing. The transceiver 216 may communicate utilizing Bluetooth, WiFi, ZigBee, Ant+, near field communications, wireless USB, infrared, mobile body area networks, ultra-wideband communications, cellular (e.g., 3G, 4G, 5G, PCS, GSM, etc.), infrared, or other suitable radio frequency standards, networks, protocols or communications. The transceiver 216 may also be a hybrid transceiver that supports a number of different communications. For example, the transceiver 216 may communicate with the computing device 204 or other systems utilizing wired interfaces (e.g., wires, traces, etc.), NFC or Bluetooth communications.

The components of the wireless earpieces 202 may be electrically connected utilizing any number of wires, contact points, leads, busses, wireless interfaces, or so forth. In addition, the wireless earpieces 202 may include any number of computing and communications components, devices or elements which may include busses, motherboards, circuits, chips, sensors, ports, interfaces, cards, converters, adapters, connections, transceivers, displays, antennas, and other similar components. The physical interface 215 is hardware interface of the wireless earpieces 202 for connecting and communicating with the computing device 204 or other electrical components, devices, or systems.

The physical interface 215 may include any number of pins, arms, or connectors for electrically interfacing with the contacts or other interface components of external devices or other charging or synchronization devices. For example, the physical interface 215 may be a micro USB port. In one embodiment, the physical interface 215 is a magnetic interface that automatically couples to contacts or an interface of the computing device 204. In another embodiment, the physical interface 215 may include a wireless inductor for charging the wireless earpieces 202 without a physical connection to a charging device.

The user interface 214 is a hardware interface for receiving commands, instructions, or input through the touch (haptics) of the user, voice commands, or predefined motions. The user interface 214 may be utilized to control the other functions of the wireless earpieces 202. The user interface 214 may include the LED array, one or more touch sensitive buttons or portions, a miniature screen or display, or other input/output components. The user interface 214 may be controlled by the user or based on commands received from the computing device 204 or a linked wireless device.

In one embodiment, the user may provide feedback by tapping the user interface 214 once, twice, three times, or any number of times. Similarly, a swiping motion may be utilized across or in front of the user interface 214 (e.g., the exterior surface of the wireless earpieces 202) to implement a predefined action. Swiping motions in any number of directions or gestures may be associated with specific activities, such as play music, pause, fast forward, rewind, activate a digital assistant (e.g., Siri, Cortana, smart assistant, etc.). The swiping motions may also be utilized to control actions and functionality of the computing device 204 or other external devices (e.g., smart, television, camera array, smart watch, etc.). The user may also provide user input by moving his head in a particular direction or motion or based on the user's position or location. For example, the user may utilize voice commands, head gestures, or touch commands to change the content displayed by the computing device 204.

The sensors 217 may include pulse oximeters, accelerometers, gyroscopes, magnetometers, inertial sensors, microphones, ear bone microphones, thermometers, photo detectors, miniature cameras, and other similar instruments for detecting location, forces or impact, orientation, motion, and so forth. The sensors 217 may also be utilized to gather optical images, data, and measurements and determine an acoustic noise level, electronic noise in the environment, ambient conditions, and so forth. The sensors 217 may provide measurements or data that may be utilized to filter or select images for display by the computing device 204. For example, motion or sound detected on the left side of the user may be utilized to command the computing device 204 to display camera images from the left side of the user. Motion or sound may be utilized, however, any number of triggers may be utilized to send commands to the computing device 204.

The computing device 204 may include components similar in structure and functionality to those shown for the wireless earpieces 202. The computing device may include any number of processors, batteries, memories, busses, motherboards, chips, transceivers, peripherals, sensors, displays, cards, ports, adapters, interconnects, and so forth. In one embodiment, the computing device 204 may include one or more processors and memories for storing instructions. The instructions may be executed as part of an operating system, application, browser, or so forth to implement the features herein described, in one embodiment, the wireless earpieces 202 may be magnetically or physically coupled to the computing device 204 to be recharged or synchronized or to be stored.

In another embodiment, the computing device 204 may also include sensors for detecting the location, orientation, and proximity of the wireless earpieces 202. For example, the computing device 204 may include optical sensors or cameras for capturing images and other content. When providing sensor information the wireless earpieces 202 may utilize and detect any number of wavelengths and spectra to provide distinct images, enhancement, data, and biometrics of the user.

As originally packaged, the wireless earpieces 202 and the computing device 204 may include peripheral devices such as charging cords, power adapters, inductive charging adapters, solar cells, batteries, lanyards, additional light arrays, speakers, smart case covers, transceivers (e.g., Wi-Fi, cellular, etc.), or so forth.

Figure 3:
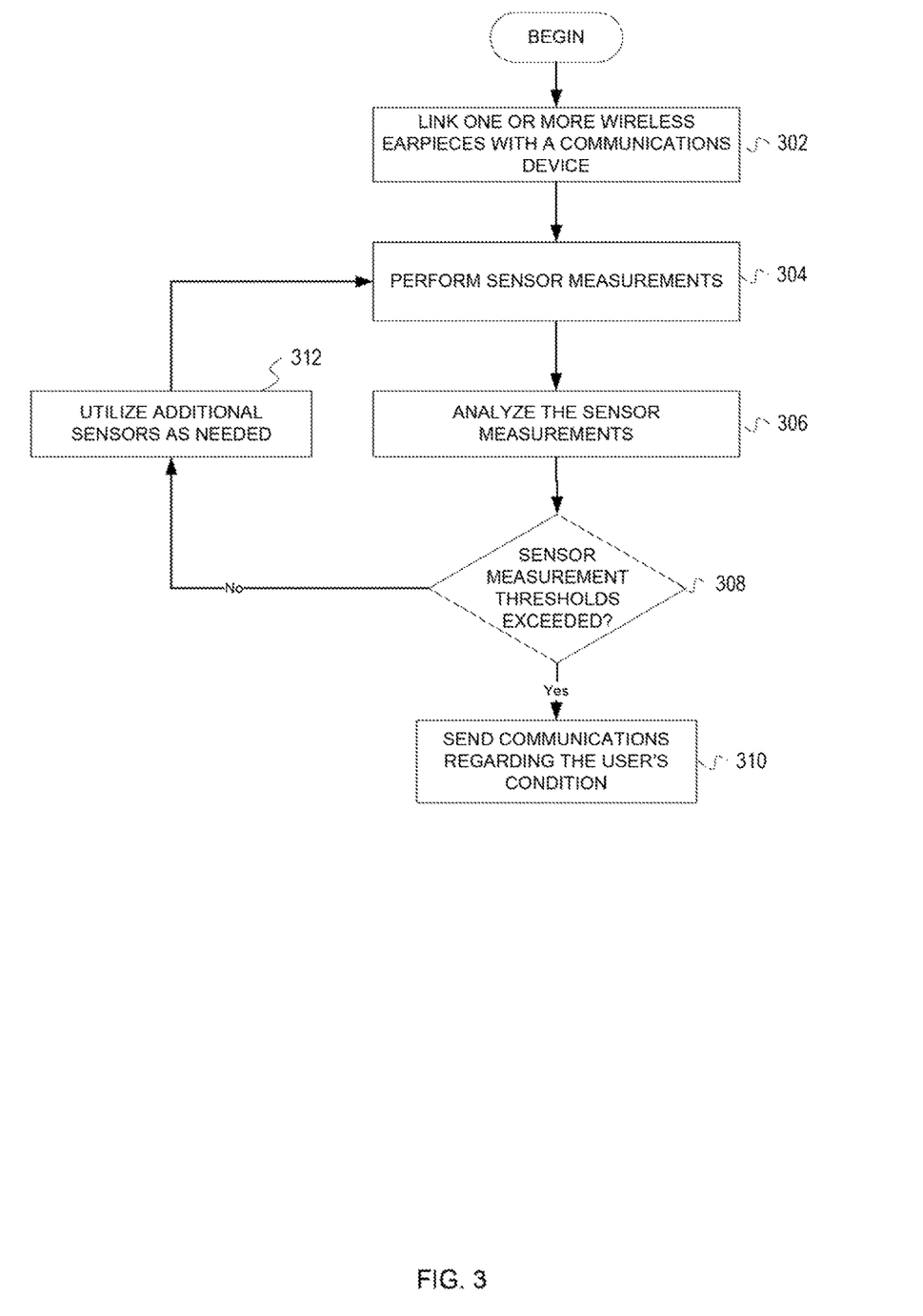
FIG. 3 is a flowchart of a process for determining users conditions utilizing wireless earpieces in accordance with an illustrative embodiment.

FIG. 3 is a flowchart of a process for determining users conditions utilizing wireless earpieces in accordance with an illustrative embodiment. The process of FIG. 3 may be implemented by one or more wireless earpieces, wearable devices, and any number of other devices communicating directly or through a personal area network.

In one embodiment, the process of FIG. 3 may begin by linking one or more wireless earpieces with a communications device (step 302). The wireless earpieces may be linked with the smart glasses utilizing any number of communications, standards, or protocols. For example, the devices may be linked by a Bluetooth connection. The process may require that the devices be paired utilizing an identifier, such as a passcode, password, serial number, voice identifier, radio frequency, or so forth. The wireless earpieces may be linked with the communications device and any number of other devices directly or through a network, such as a personal area network.

Next, the wireless earpieces perform sensor measurements (step 304). The sensor measurements may include performing any number of measurements. The measurements may be performed utilizing a predefined sampling rate (e.g., 1 second, 100 ms, etc.). The measurements may also be triggered in response to specific detected events, such as change in user orientation or position (e.g., change from vertical to horizontal position), changes in velocity (e.g., extreme starts, stops, accelerations, etc.), high forces (e.g., impacts, jolts, etc.), or detected events from other sensors worn by the user.

Next, the wireless earpieces analyze the sensor measurements (step 306). The sensor measurements may be processed or otherwise evaluated by the wireless earpieces. For example, one or more processors of the wireless earpieces may process the incoming data measurements. The sensor measurements are processed for subsequent determinations, or decisions, implemented by the wireless earpieces.

Next, the wireless earpieces determines whether sensor measurement thresholds are exceeded (step 308). The wireless earpieces may include any number of thresholds, including, high and low thresholds for measurements, such as forces experienced by the user, acceleration, temperature, pulse rate, blood oxygenation, and so forth.

In response to determining the sensor measurement thresholds are exceeded in step 308, the wireless earpieces send communications regarding the user's condition (step 310). In one embodiment, the communications are sent to the communications device linked with the wireless earpieces. For example, the communications may be an alert, status update, warning, or other similar information. In one embodiment, the communication may be an alert indicating that the user may have experienced a concussion. Likewise, the communication may indicate that the user's temperature has exceeded a threshold and may be experiencing overheating. The information from the wireless earpieces may be particularly valuable for users, such as athletes that may be playing, practicing, or competing in extreme events, conditions, or other settings. For example, the wireless earpieces may be utilized to ensure that high school football players in heat prone areas do not overexert themselves, possibly resulting in heat stroke. The communications device may be monitored by team personnel, referees, or umpires, health services groups, parents, or other monitoring groups to ensure the safety of the user.

In response to determining the sensor measurement thresholds are not exceeded in step 308, the wireless earpieces utilize additional sensors as needed (step 312). In the additional sensors may be worn, or integrated with the user. For example, additional measurements may be taken by a smart watch, or chest strap worn by the user. In another example, a pacemaker of the user may provide additional data regarding pulse, heart rhythm, and other applicable or measured information.

The illustrative embodiments provide a system, method, personal area network, and wireless earpieces for communicating sensor measurements to one or more externally connected devices. The sensor measurements are utilized to send communications, updates, alerts, or other information relative to the condition of the user as well as the user's environment. In one embodiment, the sensor measurements may be utilized to protect the user based on one or more sensor measurements that are made, such as potential head trauma, overheating, dropping body temperature, low blood oxygenation, excessive or low heart rate, or other applicable information determined by the sensors of the wireless earpieces.

The features, steps, and components of the illustrative embodiments may be combined, in any number of ways and are not limited specifically to those described. In particular, the illustrative embodiments contemplate numerous variations in the smart devices and communications described. The foregoing description has been presented for purposes of illustration and description. It is not intended to be an exhaustive list or limit any of the disclosure to the precise forms disclosed. It is contemplated that other alternatives or exemplary aspects are considered included in the disclosure. The description is merely examples of embodiments, processes or methods of the invention. It is understood that any other modifications, substitutions, and/or additions may be made, which are within the intended spirit and scope of the disclosure. For the foregoing, it can be seen that the disclosure accomplishes at least all of the intended objectives.

The previous detailed description is of a small number of embodiments for implementing the invention and is not intended to be limiting in scope. The following claims set forth a number of the embodiments of the invention disclosed with greater particularity.

What is claimed is:

1. A method for communicating utilizing a wireless earpiece having a frame shaped to fit substantially within the ear of a user, the method comprising:
    linking the wireless earpiece with a communications device using a wireless transceiver disposed within the frame;
    performing user sensor measurements of a condition of the user utilizing sensors of the wireless earpiece, the sensors disposed within the frame, and wherein the sensors include an inertial sensor for sensing inertial measurements and at least one biometric sensor for sensing biometric measurements;
    performing wearable sensor measurements of the user using one or more sensors of a wearable device other than the wireless earpiece and communicating the wearable sensor measurements to the wireless earpiece;
    performing environmental sensor measurements of an environment of the user, wherein the environmental sensor measurements include environmental audio sensed with a microphone of the wireless earpiece;
    determining at the wireless earpiece whether each of the user sensor measurements, the wearable sensor measurements, and the environmental sensor measurements exceed one or more thresholds associated with a concussion;
    logging the user sensor measurements, the wearable sensor measurements, and the environmental sensor measurements for subsequent review to a memory disposed within the frame of the wireless earpiece; and
    sending communications regarding the user sensor measurements, the wearable sensor measurements, and the environmental sensor measurements from the wireless earpiece to the communications device.

2. The method of claim 1, wherein the wireless earpieces are linked with the communications device utilizing a BLUETOOTH connection.

3. The method of claim 1, wherein a plurality of wireless earpieces communicate with the communications device to send communications regarding the condition of each of a plurality of users associated with each of the plurality of wireless earpieces.

4. The method of claim 3, wherein the plurality of users are engaged in an activity together.

5. The method of claim 1, wherein the user sensor measurements further include pulse readings performed using a pulse oximeter of the wireless earpiece.

6. The method of claim 1, further comprising:
    communicating with a plurality of users utilizing a plurality of wireless earpieces from the wireless earpiece.

7. The method of claim 1, wherein the wireless earpiece is one of a pair of wireless earpieces utilized by the user.

8. The method of claim 1, wherein the sensors further include an ear bone microphone and a thermometer.

9. The method of claim 1, wherein the wireless earpiece includes a sleeve for maintaining the wireless earpiece in the ear of the user.

* * * * *